(12) United States Patent
Tung et al.

(10) Patent No.: US 7,312,367 B2
(45) Date of Patent: *Dec. 25, 2007

(54) METHOD OF MAKING 1,1,3,3,3-PENTAFLUOROPROPENE

(75) Inventors: Hsueh Sung Tung, Getzville, NY (US); Daniel C. Merkel, West Seneca, NY (US); Rajiv R. Singh, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 29 days.

This patent is subject to a terminal disclaimer.

(21) Appl. No.: 11/452,856

(22) Filed: Jun. 14, 2006

(65) Prior Publication Data

US 2006/0235248 A1    Oct. 19, 2006

Related U.S. Application Data

(62) Division of application No. 10/671,810, filed on Sep. 26, 2003, now Pat. No. 7,091,388.

(51) Int. Cl.
*C07C 17/00* (2006.01)
*C07C 19/08* (2006.01)

(52) U.S. Cl. .............. 570/155; 570/157; 570/164; 570/166; 570/167; 570/168; 570/169

(58) Field of Classification Search .......... None
See application file for complete search history.

(56) References Cited

U.S. PATENT DOCUMENTS 5,414,165 A    5/1995    Nappa et al. ............... 570/169
5,679,875 A    10/1997   Aoyama et al. ............ 570/156
5,714,654 A    2/1998    Yamamoto et al. ......... 570/170
5,728,902 A    3/1998    Aoyama et al. ............ 570/136
5,902,912 A    5/1999    Tung et al. ................. 570/164
5,910,615 A    6/1999    Jackson et al. ............. 570/142
6,031,141 A    2/2000    Mallikarjuna et al. ...... 570/136
6,274,779 B1   8/2001    Merkel et al. ............. 570/134
6,369,284 B1   4/2002    Nappa et al. ............... 570/156
6,476,281 B2   11/2002   Qian et al. ................. 570/156
6,583,328 B1   6/2003    Qian et al. ................. 570/156

FOREIGN PATENT DOCUMENTS

WO    WO98/33754    8/1998
WO    WO99/52844    10/1999

OTHER PUBLICATIONS

Henne et al. "Fluorinated Derivatives of Propane and Propylene". Journal of the American Chemical Society, vol. 68, 1946, pp. 496-497.

*Primary Examiner*—Sikarl A. Witherspoon
(74) *Attorney, Agent, or Firm*—Roberts & Roberts, LLP

(57) ABSTRACT

The invention provides an economic process for the manufacture of the hydrofluorocarbon 1,1,3,3,3-pentafluoropropene (HFC-1225zc). HFC-1225zc can be made from the dehydrochlorination of 1-chloro-1,1,3,3,3-pentafluoropropane (HCFC-235fa). Alternatively, HFC-1225zc can also be made from the dehydrofluorination of 1,1,1,3,3,3-hexafluoropropane (HFC-236fa). HFC-1225zc) is a compound that has the potential to be used as a low Global Warming Potential refrigerant, blowing agent, aerosol propellant, or solvent.

24 Claims, No Drawings

METHOD OF MAKING 1,1,3,3,3-PENTAFLUOROPROPENE

CROSS REFERENCE TO RELATED APPLICATION

This application is a divisional of U.S. patent application Ser. No. 10/671,810 filed Sep. 26, 2003 now U.S. Pat. No. 7,091,388 which is incorporated herein by reference.

BACKGROUND OF THE INVENTION

This invention relates to a process for the manufacture of the hydrofluorocarbon 1,1,3,3,3-pentafluoropropene (HFC-1225zc). HFC-1225zc can be made from the dehydrochlorination of 1-chloro-1,1,3,3,3-pentafluoropropane (HCFC-235fa). Alternatively, HFC-1225zc can also be made from the dehydrofluorination of 1,1,1,3,3,3-hexafluoropropane (HFC-236fa). The dehydrochlorination and/or dehydrofluorination may be conducted by reaction with a caustic solution, or by thermal decomposition of HCFC-235fa and/or HFC-236fa, with or without a catalyst.

Chlorofluorocarbons (CFCs) like dichlorodifluoromethane have been used as refrigerants, blowing agents and diluents for gaseous sterilization. In recent years, there has been widespread concern that certain chlorofluorocarbons might be detrimental to the Earth's ozone layer. As a result, there is a worldwide effort to use halocarbons which contain fewer or no chlorine substituents. Accordingly, the production of hydrofluorocarbons, or compounds containing only carbon, hydrogen and fluorine, has been the subject of increasing interest to provide environmentally desirable products for use as solvents, blowing agents, refrigerants, cleaning agents, aerosol propellants, heat transfer media, dielectrics, fire extinguishing compositions and power cycle working fluids.

In this regard, 1,1,3,3,3-pentafluoropropene (HFC-1225zc) is a compound that has the potential to be used as a low GWP (Global Warming Potential) refrigerant, blowing agent, aerosol propellant, solvent, etc, and also as a fluorinated monomer. Currently this material is not available in large quantities. There is no commercially viable large scale process for manufacturing this HFC. However, the raw materials to make HFC-1225zc are readily commercially available, and this invention provides a process technology that allows for the manufacture of HFC-1225zc in large commercial scale. It is known that one can produce HFC-1225zc in a high temperature hydrogenation process using 2-chloro-1,1,3,3,3-pentachloropropene (CFC-1215) or 2,2-dichloro 1,1,3,3,3 hexafluoropropane (CFC-216) in the presence of a metal catalyst. The organic raw materials for these processes are not readily available. U.S. Pat. No. 5,714,654 has been proposed for producing 1,1,3,3,3-pentafluoropropene, in which 2-chloro-1,1,3,3,3-pentafluoropropene is hydrogenated at a temperature between 30° C. and 450° C. in the presence of a palladium, platinum and rhodium catalyst, or in which 1,1,1,3,3-pentafluoro-2,3-dichloropropane is dechlorinated by using hydrogen in the presence of a metal oxide catalyst. U.S. Pat. No. 6,369,284 provides a process for producing 1,1,3,3,3-pentafluoropropene (HFC-1225zc) from 1,1,1,3,3,3-hexafluoropropane (HFC-236fa). In accordance with this patent, HFC-236fa is dehydrofluorinated to HFC-1225zc over a catalyst at a temperature of from about 200° C. to 500° C. The catalyst system is a combination of oxides, fluorides and oxyfluorides of magnesium, zinc and mixtures of magnesium and zinc, lanthanum fluoride, fluorided lanthanum oxide, and three-dimensional matrix carbonaceous material. U.S. Pat. No. 6,031,141 also shows a process for producing HFC-1225zc from HFC-236fa using a cubic chromium trifluoride catalyst.

It has been determined that these known processes are not economical relative to their product yield. Accordingly, the present invention provides an alternate process for forming HFC-1225zc which is more economical than prior art processes and a higher yield process as compared to known processes. In particular, it has now been found that HFC-1225zc may be formed by dehydrochlorination of HCFC-235fa using caustic or thermal decomposition optionally in the presence of a catalyst for HCl removal. Alternatively, HFC-1225zc may be formed by dehydrofluorination of HFC-236fa using caustic or thermal decomposition optionally in the presence of a catalyst for HF removal.

DESCRIPTION OF THE INVENTION

The invention provides a process for the manufacture of 1,1,3,3,3-pentafluoropropene comprising reacting a reactant comprising at least one of 1-chloro-1,1,3,3,3-pentafluoropropane and 1,1,1,3,3,3-hexafluoropropane with a caustic solution under conditions sufficient to dehydrochlorinate 1-chloro-1,1,3,3,3-pentafluoropropane and/or to dehydrofluorinate 1,1,1,3,3,3-hexafluoropropane, to form a reaction product which comprises 1,1,3,3,3-pentafluoropropene.

The invention also relates to a process for the manufacture of 1,1,3,3,3-pentafluoropropene comprising thermally decomposing a reactant comprising at least one of 1-chloro-1,1,3,3,3-pentafluoropropane and 1,1,1,3,3,3-hexafluoropropane, under conditions sufficient to dehydrochlorinate 1-chloro-1,1,3,3,3-pentafluoropropane and/or to dehydrofluorinate 1,1,1,3,3,3-hexafluoropropane, to form a reaction product which comprises 1,1,3,3,3-pentafluoropropene and wherein the decomposing is conducted either without a catalyst or with a catalyst selected from the group consisting of transition metal halides and oxides and combinations thereof, preferably iron halides, nickel halides, cobalt halides and combinations thereof.

The preferred starting organic material for the present method is 1-chloro-1,1,3,3,3-pentafluoropropane (HCFC-235fa) which can be produced by many art known methods. HCFC-235fa can be made from the incomplete fluorination of 1,1,1,3,3,3-hexachloropropane (HCC-230fa) in the liquid phase and/or gas phase as described in EPO publication 0 522 639 A1, U.S. Pat. No. 5,395,997 and U.S. Pat. No. 6,187,976. HCC-230fa is a commercially available material. Alternatively, HCFC-235fa can be made via the photochlorination of 1,1,1,3,3-pentafluoropropane HFC-245fa as described in U.S. Pat. No. 6,551,469.

The alternate organic starting material for the present method is 1,1,1,3,3,3 hexafluoropropane HFC-236fa which can be dehydrofluorinated to produce HFC-1225zc. HFC-236fa can be prepared by numerous methods, e.g. as described in U.S. Pat. Nos. 5,395,997; 5,414,165; and WO96/15085-A1. It is also available commercially from several fluorocarbon manufacturers in commercial quantities at relatively low cost.

In another embodiment of the invention, HCFC-235fa and/or HFC-236fa can be prepared by fluorinating 1,1,1,3,3,3-hexachloropropane (HCC-230). In this embodiment, in a preliminary step, the process of the invention involves the formation of HCFC-235fa and/or HFC-236fa by reacting 1,1,1,3,3,3-hexachloropropane (HCC-230) with hydrogen fluoride (HF) in the vapor phase, or the liquid phase, preferably in the presence of a fluorination catalyst as is well known in the art.

The result is a reaction product of one or both of the two products, HCFC-235fa and/or HFC-236fa. In the preferred embodiment of the invention, the HF to HCC-230fa mole ratio preferably ranges from about 2:1 to about 100:1; more preferably from about 5:1 to about 50:1 and most preferably from about 6:1 to about 20:1.

Useful fluorination catalysts include, but are not limited to, transition metal halides, Group IVb and Vb metal halides, and combinations thereof, preferably supported on activated carbon or fluorinated alumina. These catalysts are typically employed in an amount of from about 1 wt. % to about 90 wt. % based on the total weight of catalyst and support. More specifically, preferred vapor phase fluorination catalysts non-exclusively include $SbCl_5$, $SbCl_3$, $SbF_5$, $TaCl_5$, $SnCl_4$, $NbCl_5$, $TiCl_4$, $MoCl_5$, $Cr_2O_3$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Preferred liquid phase fluorination catalysts non-exclusively include $SbCl_5$, $SbCl_3$, $SbF_5$, $TaCl_5$, $SnCl_4$, $NbCl_5$, $TiCl_4$, and $MoCl_5$. It is understood that after pre-treatment with HF or during reaction in the presence of HF the above mentioned catalyst will be partially fluorinated. Chromium oxide/aluminum oxide catalysts are described in U.S. Pat. No. 5,155,082 which is incorporated herein by reference. Chromium (III) oxides such as crystalline chromium oxide or amorphous chromium oxide are preferred vapor phase fluorination catalysts with amorphous chromium oxide being the most preferred vapor phase catalyst. Chromium oxide ($Cr_2O_3$) is a commercially available material which may be purchased in a variety of particle sizes. Unsupported $SbCl_5$ and $SbCl_3$ halides are preferred liquid phase catalysts. Both of these liquid phase catalysts are commercially available and well known in the art. Fluorination catalysts having a purity of at least 98% are preferred. The fluorination catalyst is present in an amount sufficient to drive the reaction. The fluorination reaction may be conducted in any suitable fluorination reaction vessel or reactor but it should preferably be constructed from materials which are resistant to the corrosive effects of hydrogen fluoride such as nickel and its alloys, including Hastelloy, Inconel, Incoloy, and Monel or vessels lined with fluoropolymers.

Any water in the hydrogen fluoride (HF) will react with and deactivate the fluorination catalyst. Therefore substantially anhydrous hydrogen fluoride is preferred. By "substantially anhydrous" it is meant that the HF contains less than about 0.05 weight % water, preferably contains less than about 0.02 weight % water and most preferably less than about 0.005 weight %. Such is commercially available from Honeywell International Inc. or Air Products and Chemicals, Inc. However, one of ordinary skill in the art will appreciate that the presence of water in the HF can be compensated for by increasing the amount of catalyst used.

The liquid phase fluorination of HCC-230 is preferably conducted at a temperature of from about 50° C. to about and 450° C., more preferably from about 60° C. to about 180° C. and most preferably from about 65° C. and 150° C. Liquid phase fluorination is preferably conducted at a pressure of from about 50 psig to about 400 psig, preferably from about 60 psig to about 200 psig. The reactor is preferably preheated to the desired fluorination reaction temperature while or before anhydrous HF is fed to the reactor. The HCC-230 and HF may be fed to the reactor at the desired temperatures and pressures that are described herein. In a preferred embodiment of the invention, either or both of the HCC-230 and HF are pre-vaporized or preheated prior to entering the reactor.

When HCC-230 and HF are reacted in a vapor phase with the fluorination catalyst the HCC-230 and HF may be fed to the reactor at the desired temperatures and pressures that are described herein The reactor is preheated to the fluorination reaction temperature while or before anhydrous HF is fed to the reactor. The HCC-230fa and HF may be fed to the reactor at any convenient temperature and pressure. In a preferred embodiment either or both of the HCC-230fa and HF are pre-vaporized or preheated to a temperature of from about 30° C. to about 300° C. prior to entering the reactor. In another embodiment, the HCC-230fa and HF are vaporized in the reactor.

The vapor phase fluorination reaction is conducted at a preferred temperature ranging from about 80° C. to about 400° C.; more preferably from about 100° C. to about 350° C. and most preferably from about 200° C. to about 330° C. Reactor pressure is not critical and can be superatmospheric, atmospheric or under vacuum. Vapor phase fluorination is preferably conducted at a pressure of from about 0 psig to about 400 psig, more preferably from about 50 psig to about 200 psig. When vapor phase fluorination is conducted under vacuum, the pressure can be from about 5 torr to about 760 torr. The reactant vapor is allowed to contact the fluorination catalyst for from about 0.01 to about 240 seconds, more preferably from about 0.1 to about 60 seconds and most preferably from about 0.5 to about 20 seconds. The reaction is preferably conducted in a continuous mode but may be conducted in a batch mode.

Usually the process flow of the HCC-230 and HF is in the down direction through a bed of the catalyst. Before each use, the catalyst is preferably dried, pre-treated and activated. It may also be advantageous to periodically regenerate the catalyst after prolonged use while in place in the reactor. For $Cr_2O_3$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ catalysts, pre-treatment can be done by heating the catalyst to about 250° C. to about 430° C. in a stream of nitrogen or other inert gas. The catalyst may then be activated by treating it with a stream of HF diluted with a large excess of nitrogen gas in order to obtain high catalyst activity. Regeneration of the catalyst may be accomplished by any means known in the art such as, for example, by passing air or air diluted with nitrogen over the catalyst at temperatures of from about 100° C. to about 400° C., preferably from about 200° C. to about 375° C., for from about 1 hour to about 3 days, depending on the size of the reactor. For $SbCl_5$, $SbCl_3$, $TaCl_5$, $SnCl_4$, $NbCl_5$, $TICl_4$, $MoCl_5$ catalysts, supported on an solid support such as activated carbon, pre-treatment or activation can be done by first heating the catalyst to about 30° C. to 250° C. in a stream of nitrogen or other inert gas. It is then treated with a stream of HF in the absence or presence of an oxidizing agent such as chlorine gas in order to obtain high catalyst activity. In addition, the catalyst may optionally be kept active by co-feeding chlorine to the reactor during reaction. The chlorine is fed to the fluorination reaction in an amount of from about 0.1 mol % to about 10 mol % based on the sum of the quantity of 1,1,1,3,3,3-hexachloropropane (HCC-230) and recyled intermediates.

HCFC-235fa and HFC-236fa may be recovered from the fluorination reaction product mixture comprised of unreacted starting materials and by-products, including HCl, by any means known in the art, such as by scrubbing, extraction, and preferably distillation. For example, the distillation may be preferably conducted in a standard distillation column at a pressure, which is less than about 300 psig, preferably less than about 150 psig and most preferably less than 100 psig. The pressure of the distillation column inherently determines the distillation operating temperature. HCl may be recovered by operating the distillation column at from about −40° C. to about 25° C., preferably from about −40° C. to about −20° C. Single or multiple distillation columns may be used. The distillate portion includes substantially all the HCFC-235fa, HFC-236fa, unreacted HF and HCl produced in the reaction as well as any other impurities. In the preferred embodiment, HCFC-235fa and the HFC-236fa are separated from all other reaction by-products and unreacted HF for further reaction in step (b) described herein. In the preferred embodiment, any HF present may also be recovered and recycled back for subsequent fluorination reactions.

Dehydrochlorination and dehydrofluorination chemistries are well known in the art and show a high selectivity for the desired product. Using the process of this invention to manufacture HFC-1225zc is safer, more economical, and versatile than the prior art methods. As the reaction formulas below illustrate, HFC-1225zc is formed by the dehydrochlorination of 1-chloro-1,1,3,3,3-pentafluoropropane (HCFC-235fa) or the dehydrofluorination of 1,1,1,3,3,3-hexafluoropropane (HFC-236fa).

In one embodiment of the invention, the dehydrochlorination of HCFC-235fa and dehydrofluorination of HFC-236fa are accomplished by reacting these with a strong caustic solution that includes, but is not limited to KOH, NaOH, Ca(OH)$_2$ and CaO at an elevated temperature. These reactions proceed, for example, as follows:

CClF$_2$—CH$_2$—CF$_3$→CF$_3$—CH=CF$_2$+HCl

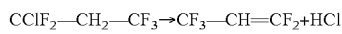
(HCFC-235fa) (HFC-1225zc)

The dehydrochlorination reaction can be achieved by using caustic for HCl removal or by thermal decomposition in the absence of a catalyst or with a catalyst selected from the group consisting of transition metal halides and oxides and combination thereof, preferably iron halides, nickel halides, cobalt halides and combinations thereof.

CF3—CH2—CF3→CF3—CH=CF2+HF

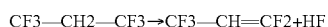
(HFC-236fa) (HFC-1225zc)

The dehydrofluorination reaction can be achieved by using caustic for HF removal or by thermal decomposition optionally in the presence of a catalyst.

Dehydrochlorination and dehydrofluorination reactions are well known in the art. In the preferred embodiment of the invention, the caustic strength of an aqueous caustic solution is of from about 2 wt % to about 100 wt %, more preferably from about 5 wt % to about 90 wt % and most preferably from about 10 wt % to about 80 wt %. 100 wt. % caustic is in solid form. The reaction is preferably conducted at a temperature of from about 20° C. to about 150° C., more preferably from about 30° C. to about 110° C. and most preferably from about 40° C. to about 90° C. The reaction pressure is not critical and may be conducted at atmospheric pressure, super-atmospheric pressure or under vacuum. Superatmospheric pressures are preferred and may be about 400 psia or less, and preferably about 200 psia or less. The vacuum pressures can be from about 5 torr to about 760 torr, preferably from about 500 torr to about 760 torr. In addition, a solvent may optionally be used to help dissolve the organic compounds in the caustic solution. This optional step may be conducted using solvents that are well known in the art for said purpose. Non-exclusive examples of such solvents are polar solvents, such as alcohols and nitriles like acetonitrile.

In an alternate embodiment of the invention, the dehydrochlorination of HCFC-235fa and dehydrofluorination of HFC-236fa may be done by thermal decomposition optionally in the presence of a catalyst. Suitable catalysts include transition metal halides and oxides, supported or bulk. Preferred catalyst include, but are not limited to, FeCl$_3$, NiCl$_2$, CoCl$_2$, supported or in bulk. The preferred temperatures for the thermal decomposition are from about 30° C. to about 400° C., more preferably from about 50° C. to about 350° C. and most preferably from about 75° C. to about 300° C. As above, the reaction pressure is not critical and may be conducted at atmospheric pressure, super-atmospheric pressure or under vacuum. Superatmospheric pressures are preferred and may be about 400 psia or less, and preferably about 200 psia or less. The vacuum pressures can be from about 5 torr to about 760 torr, preferably from about 500 torr to about 760 torr.

The reactions may be conducted in any suitable reactor. Further, the dehydrochlorination of HCFC-235fa and the dehydrofluorination of HFC-236fa may either be conducted simultaneously in the same reactor, or mixtures of HCFC-235fa and HFC-236fa may first be separated followed by separately dehydrochlorinating HCFC-235fa with the caustic solution or by thermal decomposition and separately dehydrofluorinating HFC-236fa with the caustic solution or by thermal decomposition. The result of this two step process is a high yield of HFC-1225zc. Thereafter the resulting 1,1,3,3,3-pentafluoropropene may be purified, such as by washing it with a caustic solution, drying and distilling.

The following non-limiting examples serve to illustrate the invention.

EXAMPLE 1

To a reaction setup consisting of a 3-neck round bottom flask (5 L), mechanical agitator, reflux condenser, and low temperature cold trap is added 3000 ml acetonitrile and 9.9 moles (504 g) of KOH pellets. After mixing, 4 moles (673 grams) of 1-chloro-1,1,3,3,3-pentafluoropropane (HCFC-235fa) is added through a dip leg. The reagents were heated slowly with vigorous agitation. Reaction is observed at relatively low temperatures. The crude product is collected in the cold trap. The crude material collected consisted of a good yield of HFC-1225zc.

EXAMPLE 2

Example 1 is repeated except HFC-236fa is used instead of HCFC-235fa. 4 moles (608 grams) of HFC-236fa is added to the acetonitrile/caustic solution through the dip tube. The reagents were heated slowly with vigorous agitation. Reaction is observed at higher temperatures than in Example 1. The crude product is collected in the cold trap. The crude material collected consisted of a good yield of HFC-1225zc.

EXAMPLE 3

540 grams of 15.3 wt % KOH solution and 100 grams of a mixture of 1-chloro-1,1,3,3,3-pentafluoropropane (HCFC-235fa) [66.8 GC area %] and 1,1,1,3,3,3-hexafluoropropane (HFC-236fa) [28.3 GC area %], with a minor amount of impurities, were added to a 1.0 liter SS cylinder. The cylinder was slowly heated to 110-120° C. and shaken for five (5) hours. A sample of the vapor space showed a high concentration of the desired product, HFC 1225zc. A sample of the organic liquid layer showed <20% of the starting organic was left unreacted.

EXAMPLE 4

Liquid Phase Conversion of HCC-230

A 50 gal. Fluoropolymer lined reactor was charged with 300 lbs of liquid $SbCl_5$ fluorination catalyst. The reactor was equipped with a 6"D×8'L catalyst stripper containing structured packing and reflux condenser. The catalyst was first fluorinated by adding a sufficient amount of Hydrogen Fluoride (HF). The reactor was heated to 80-95° C. and brought to a pressure of 150-180 psig. Gaseous HF was fed to the reactor continuously at a rate of 14-15 lb/hr through a sparger and liquid 1,1,1,3,3,3-hexachloropropane (HCC-230) was fed continuously at a rate of 20-23 lb/hr. $Cl_2$ was continuously added to the reaction mixture to keep the catalyst active at 1.6-1.7 lb/hr. The gas exiting the reflux condenser was passed through a scrubber that contained KOH solution to remove excess HF and the HCl that was generated during the reaction. 431 lbs of the crude product was collected after the scrubber and was analyzed by GC. The following is the analysis of the major component of the crude product in GC area %. Note the presence of the HFC 1225zc after the material was passed through the scrubber containing KOH solution.

| Component | Area % |
| --- | --- |
| HFC-1225zc | 4.1 |
| HFC-236fa | 68.7 |
| CFC-1215xc | 2.1 |
| HCFC-235fa | 23.5 |

EXAMPLE 5

Vapor Phase Fluorination of HCC-230

About 132 g (about 1.33 g/cc bulk density) of a chromium (III) oxide catalyst, is charged to a reactor of 1" diameter Monel pipe. The catalyst was dried and pretreated with HF before use.

The reactor is preheated to the reaction temperature of about 300° C. while anhydrous HF is fed to the reactor. An organic feed (HCC-230) is started when the reactor reaches the desired temperature and pressure. The HF and organic feeds are then adjusted to the desired rates. HCFC-235fa and HFC-236fa are found in the reactor effluent product stream, along with other partially fluorinated species such as HFC-1225zc and CFC-1215xc.

EXAMPLE 6

In a typical experiment, a 2.54 cm×81 cm Monel® reactor is used. About 500 ml of $FeCl_3$ catalyst supported on activated carbon was packed into the reactor. The reactor was heated to 150° C. under 1 liter/hr of nitrogen flow to dry the catalyst for 4 hours. Then, the reactor temperature is brought to 250° C. under the same nitrogen flow and 235fa is fed to the reactor at 1 g/min, and in the mean time the nitrogen flow is stopped. HFC-1225zc was found by using the in-line GC at the outlet of the reactor at 95% selectivity and 85% single pass conversion.

EXAMPLE 7

The same experiment described in Example 6 is repeated, except that 236fa is used as feed. At the outlet of the reactor, 1225zc is found at 95% selectivity and 75% single pass conversion.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for the manufacture of 1,1,3,3,3-pentafluoropropene comprising
   a) reacting 1,1,1,3,3,3-hexachloropropane with hydrogen fluoride, in the presence of a fluorination catalyst to thereby produce a product comprising 1,1,1,3,3,3-hexafluoropropane and optionally additionally 1-chloro-1,1,3,3,3-pentafluoropropane; and then
   b) reacting the 1,1,1,3,3,3-hexafluoropropane and optionally additionally 1-chloro-1,1,3,3,3-pentafluoropropane, with a caustic under conditions sufficient to dehydrofluorinate 1,1,1,3,3,3-hexafluoropropane and optionally additionally dehydrochlorinate 1-chloro-1,1,3,3,3-pentafluoropropane, to form a reaction product which comprises 1,1,3,3,3-pentafluoropropene.

2. The process of claim 1 further comprising the subsequent step of purifying the resulting 1,1,3,3,3-pentafluoropropene from the reaction product.

3. The process of claim 1 wherein the product of step a) and the reactant of step b) do not comprise 1-chloro-1,1,3,3,3-pentafluoropropane.

4. The process of claim 1 wherein the product of step a) and the reactant of step b) comprise both 1-chloro-1,1,3,3,3-pentafluoropropane and 1,1,1,3,3,3-hexafluoropropane.

5. The process of claim 1 wherein the product of step a) comprises both 1-chloro-1,1,3,3,3-pentafluoropropane and 1,1,1,3,3,3-hexafluoropropane and said dehydrochlorination of 1-chloro-1,1,3,3,3-pentafluoropropane and said dehydrofluorination of 1,1,1,3,3,3-hexafluoropropane are conducted simultaneously in the same reactor.

6. The process of claim 1 wherein the 1,1,1,3,3,3-hexafluoropropane and optional 1-chloro-1,1,3,3,3-pentafluoropropane are prepared by reacting 1,1,1,3,3,3-hexachloropropane with hydrogen fluoride in a vapor phase.

7. The process of claim 6 wherein said fluorination catalyst comprises transition metal halides, Group IVb metal halides, Group Vb metal halides or combinations thereof on activated carbon or fluorinated alumina.

8. The process of claim 1 wherein the 1,1,1,3,3,3-hexafluoropropane and optional 1-chloro-1,1,3,3,3-pentafluoropropane are prepared by reacting 1,1,1,3,3,3-hexachloropropane with hydrogen fluoride in a liquid phase.

9. The process of claim 8 wherein said fluorination catalyst comprises transition metal halides, Group IVb metal halides, Group Vb metal halides or combinations thereof.

10. The process of claim 6 further comprising feeding chlorine to the step a) reaction.

11. The process of claim 8 further comprising feeding chlorine to the step a) reaction.

12. A process for the manufacture of 1,1,3,3,3-pentafluoropropene comprising
   a) reacting 1,1,1,3,3,3-hexachloropropane with hydrogen fluoride in the presence of a fluorination catalyst to thereby produce a product comprising at least one of 1,1,1,3,3,3-hexafluoropropane and 1-chloro-1,1,3,3,3-pentafluoropropane; and then
   b) thermally decomposing the 1-chloro-1,1,3,3,3-pentafluoropropane and/or 1,1,1,3,3,3-hexafluoropropane, under conditions sufficient to form a reaction product which comprises 1,1,3,3,3-pentafluoropropene and wherein the decomposing is optionally conducted with a catalyst comprising supported transition metal halides supported transition metal oxides, bulk transition metal oxides, or combinations thereof.

13. The process of claim 12, wherein the step b) catalyst comprises iron halides, nickel halides, cobalt halides or combinations thereof.

14. The process of claim 12 wherein 1-chloro-1,1,3,3,3-pentafluoropropane is decomposed to form a reaction product which comprises 1,1,3,3,3-pentafluoropropene.

15. The process of claim 12 wherein 1,1,3,3,3-hexafluoropropane is decomposed to form a reaction product which comprises 1,1,3,3,3-pentafluoropropene.

16. The process of claim 12 wherein both 1-chloro-1,1,3,3,3-pentafluoropropane and 1,1,1,3,3,3-hexafluoropropane are decomposed to form a reaction product which comprises 1,1,3,3,3-pentafluoropropene.

17. The process of claim 15 wherein said 1-chloro-1,3,3,3-tetrafluoropropane and said of 1,1,1,3,3,3-hexafluoropropane are decomposed simultaneously in the same reactor.

18. The process of claim 12 wherein step b) is conducted in the presence of the catalyst.

19. The process of claim 12 wherein the 1,1,1,3,3,3-hexafluoropropane and optional 1-chloro-1,1,3,3,3-pentafluoropropane are prepared by reacting 1,1,1,3,3,3-hexachloropropane with hydrogen fluoride in a liquid phase.

20. The process of claim 19 wherein said fluorination catalyst comprises transition metal halides, Group IVb metal halides, Group Vb metal halides or combinations thereof.

21. The process of claim 12 further comprising feeding chlorine to the step a) reaction.

22. The process of claim 12 wherein the 1,1,1,3,3,3-hexafluoropropane and optional 1-chloro-1,1,3,3,3-pentafluoropropane are prepared by reacting 1,1,1,3,3,3-hexachloropropane with hydrogen fluoride in a vapor phase.

23. The process of claim 22 wherein hydrogen fluoride resulting from the dehydrofluorination of 1,1,1,3,3,3-hexafluoropropane is recycled to the reaction of fluorinating 1,1,1,3,3,3-hexachloropropane.

24. The process of claim 22 further comprising feeding chlorine to the step a) reaction.

* * * * *